United States Patent [19]

Stapp

[11] 3,954,842

[45] May 4, 1976

[54] PROCESS FOR THE PRODUCTION OF UNSATURATED ESTERS

[75] Inventor: Paul R. Stapp, Bartlesville, Okla.

[73] Assignee: Phillips Petroleum Company, Bartlesville, Okla.

[22] Filed: May 29, 1974

[21] Appl. No.: 474,253

[52] U.S. Cl. .................. 260/476 R; 260/465 D; 260/465.4; 260/468 R; 260/468 K; 260/475 F; 260/475 N; 260/484 A; 260/485 F; 260/485 H; 260/485 L; 260/485 N; 260/491
[51] Int. Cl.$^2$ .................. C07C 67/00; C07C 67/03
[58] Field of Search ............... 260/476 R, 491

[56] References Cited
UNITED STATES PATENTS

| | | |
|---|---|---|
| 2,446,114 | 7/1948 | Strassburg.................. 260/491 X |
| 3,631,079 | 12/1971 | Sennewald et al.......... 260/476 R X |
| 3,652,656 | 3/1972 | Heywood et al............ 260/491 X |
| 3,840,588 | 10/1974 | Pearson...................... 260/476 R X |

*Primary Examiner*—Richard L. Raymond

[57] ABSTRACT

The thermal reaction of olefinic reactants with formaldehyde in saturated esters as solvent provides a convenient one-step preparation of unsaturated esters. The unsaturated ester products can be pyrolyzed to isoprene or used as chemical intermediates and in flavors and fragrances.

5 Claims, No Drawings

PROCESS FOR THE PRODUCTION OF UNSATURATED ESTERS

This invention relates to the production of unsaturated esters. In accordance with another aspect, this invention relates to the condensation of olefinic reactants with formaldehyde in the presence of saturated esters as solvents. In accordance with a further aspect, this invention relates to a one-step process for the preparation of unsaturated esters by the thermal condensation of olefinic reactants in the presence of saturated esters as solvent.

The reaction of olefins with formaldehyde is known. Various expedients have been advanced to improve the yield of desired products or to alter the reaction to produce other more useful products. In accordance with the invention, it has been found that unsaturated esters can be produced from the condensation of olefinic reactants with formaldehyde when saturated esters are used as reaction solvents.

Accordingly, an object of this invention is to provide an improved olefinic reactant-formaldehyde condensation process.

Another object of this invention is to provide a one-step process for the preparation of unsaturated esters.

In accordance with another object, this invention relates to a process for the production of high yields of unsaturated esters.

Other objects, aspects, as well as the several advantages of the invention will be apparent to those skilled in the art upon reading the specification and the appended claims.

In accordance with the invention, a process is provided for the production of unsaturated esters comprising contacting an olefinic reactant with formaldehyde in the presence of saturated esters as reaction solvent.

More specifically, it has been found that the thermal reaction of olefinic reactants, such as those having from 3 to 20 carbon atoms per molecule, with formaldehyde in saturated esters as reaction solvent is a practical one-step preparation of unsaturated esters which materals can be pyrolyzed to conjugated diolefins, such as isoprene or used as chemical intermediates and in flavors and fragrances.

In accordance with one specific embodiment, 3-methyl-3-buten-1-yl-benzoate, is produced from the reaction of isobutylene, paraformaldehyde, and methyl benzoate.

In another specific embodiment, 3-methyl-3-buten-1-yl formate is produced by the reaction of isobutylene with formaldehyde in methyl formate.

In accordance with a further specific embodiment, 3-buten-1-yl acetate is produced by the reaction of propylene with paraformaldehyde in ethyl acetate.

Olefinic reactants suitable for reacting with formaldehyde in the presence of an ester diluent must have at least one allylic hydrogen atom in the molecule. However, certain substituent groups may be present in the olefinic reactant molecule if they are attached to a carbon atom which is at least two carbon atoms removed from a carbon atom of the double bond. Examples of such substituent groups which may be present include —CN, —CO₂CH₃, —Cl, —F, and —O—CH₃. Suitable olefinic reactants contain from 3–20 carbon atoms per molecule. Examples of suitable olefinic reactants include propylene, isobutylene, α-methyl styrene, 1-butene, 1-methylocyclohexene, 2,4,4-trimethyl-1-pentene, isoprene and the like. Other examples of suitable olefinic reactants include 5-hexenenitrile methyl 5-hexenoate, 5-chloro-1-pentene, 6-fluoro-1-hexene, methyl 4-pentenyl ether and the like.

The aldehyde employed in the instant invention is formaldehyde. However, the formaldehyde can be employed in any of its various known forms such as 1,3,5-trioxane, paraformaldehyde and the like. It is also possible to employ aqueous formaldehyde solutions such as the readily available formalin which contains 35–40% formaldehyde usually with a small amount of methanol also present.

The ester which is a reactant and also a diluent in the reaction of this invention can be described by the general formula

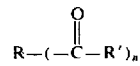

wherein $n$ is an integer of 1 or 2 and wherein if $n$ is 1, R can be hydrogen, a hydrocarbon radical such as alkyl, aryl, cycloalkyl or combinations thereof such as alkaryl and the like and wherein if $n$ is 2, R is a divalent hydrocarbon radical such as alkylene, arylene, or cycloalkylene radical or combinations such as aralkylene, alkarylene and the like wherein if R is not hydrogen the radical contains from 1–12 carbon atoms. R' in said general formula contains from 1–10 carbon atoms and is selected from primary hydrocarbyl radicals such as alkyl, aralkyl or cycloalkylalkyl. Methyl, ethyl, 1-propyl, 1-butyl, 1-hexyl, benzyl, 2-phenyl-1-ethyl, 4-cyclohexyl-1-butyl and the like are examples of R'.

Examples of suitable esters include methyl benzoate, methyl formate, ethyl acetate, diethyl succinate, benzyl octanoate, 2-phenyl-1-ethyl acetate and the like.

In actual operation, the instant reaction is carried out ordinarily at a temperature in the range of from about 50° to about 350°C, preferably from about 200° to about 300°C. The time period for the instant invention is generally from 30 seconds up to as long as several days but preferably from 10 minutes to 4 hours.

Generally, the pressure employed for the reaction of this invention is simply that generated by the reactants at the temperature employed (autogenous pressure). However, for reactions which involve the higher molecular weight olefins and/or ester reactants, it may be desirable to employ an inert gas such as nitrogen under several hundred pounds pressure in order to keep a high concentration of formaldehyde in the liquid phase.

The molar ratio of olefin reactant to formaldehyde (as CH₂O) should be at least 1/1 but is limited at the upper end only by considerations of practicality and reasonableness. Preferably, the ratio will be in the range of from 5/1 to 10/1.

The molar ratio of ester reactant to formaldehyde (as CH₂O) should be at least 0.5/1 and is limited at the upper end only by considerations of practicality and reasonableness. Preferably, this ratio will be within the range of from 2/1 to 10/1.

The unsaturated esters which are the products of the instant invention can be recovered from the reaction mixture by conventional methods such as fractional crystallization and/or fractional distillation.

The unsaturated esters of this invention can be pyrolyzed to form conjugated diolefins in accordance with known pyrolysis procedures for esters. Many of the unsaturated ester products of this invention possess distinctive odors which make them suitable for use in the field of flavors and fragrances.

Examples of unsaturated esters which can be produced by the instant invention include
3-methyl-3-buten-1-yl benzoate,
3-methyl-3-buten-1-yl formate,
3-methyl-3-buten-1-yl acetate,
3-buten-1-yl acetate and the like.

EXAMPLE I

A control run was carried out which demonstrates that the direct esterification of unsaturated alcohols with organic acids is often a very poor method of obtaining the corresponding unsaturated ester.

A 500 ml round bottom flask equipped with reflux condenser was charged with 138 g (3.0 mols) of 96% (or greater) formic acid and 43 g (0.5 mol) of 3-methyl-3-buten-1-ol. This reaction mixture was refluxed for 6 hours. The reaction mixture was then mixed with 500 ml water and extracted four times with 200 ml portions of ether. The combined ether extracts were washed with $Na_2CO_3$ until neutral, dried over $MgSO_4$, filtered, and the ether distilled away. The residue was then fractionally distilled under reduced pressure.

| Fraction No. | Boiling Range, °C | Pressure mm Hg | Weight Grams |
|---|---|---|---|
| 1 | 39–43 | 18 | 0.7 |
| 2 | 4–110 | 0.2 | 6.0 |
| 3 | 110–152 | 0.2 | 7.8 |
| Residue | — | — | 19.8[a] |

[a] Viscous tarry material.

Since the boiling point of the expected 3-methyl-3-buten-1-yl formate is 146°C at 760 mm Hg, fraction 1 would be expected to comprise the ester produced by this direct esterification method. As can be seen from the weight of said fraction 1, the amount of desired ester produced was very low indeed.

EXAMPLE II

A one liter autoclave was charged with 22 g (0.68 mol) of 92.8% paraformaldehyde, 250 ml (273 g, 2.0 mol) methyl benzoate, and 295 g (5.27 mol) isobutylene. The reactor was heated at 275°C for 45 minutes. The reactor was cooled, vented, opened and the contents filtered into a distilling flask using a little benzene. The mixture was then fractionally distilled employing a 15 inch Vigreaux column.

| Fraction No. | Boiling Range, °C | Pressure, mm Hg | Weight grams |
|---|---|---|---|
| 1 | 57–135 | atmospheric | 26.0 |
| 2 | 42–77 | 12 | 28.1 |
| 3 | 77–85 | 12 | 210.3 |
| 4 | 85–128 | 12 | 14.0 |
| 5 | 128–135 | 12 | 44.6[a] |
| Residue | — | — | 3.5 |

[a] Essentially pure 3-methyl-3-buten-1-yl benzoate.

Analysis of the five fractions by GLC procedures showed that the product mixture was comprised of:

| | |
|---|---|
| Methanol | 3.93 g |
| 3-Methyl-3-buten-1-ol | 24.51 g |
| Methyl benzoate (recovered) | 232.2 g |
| 3-Methyl-3-buten-1-yl benzoate | 45.9 g |

The material identified as 3-methyl-3-buten-1-yl benzoate was confirmed as to its identity by elemental analysis for carbon (calc. 75.8%, found 75.49%) and hydrogen (calc. 7.4%, found 7.9%) and by nuclear magnetic resonance analysis. Based on the amount of formaldehyde charged the yield of the unsaturated ester was 35.6% of the theoretical yield.

EXAMPLE III

A one liter autoclave was charged with 16 g (0.495 mol) of 92.8% paraformaldehyde, 200 ml (195 g, 3.25 mols) of methyl formate and 301 g (5.375 mols) of isobutylene. The reactor was heated to 275°C for 30 minutes (pressure was 3650 psig). The autoclave was cooled, vented, opened and the contents transferred, using a little benzene, to a distillation flask. The mixture was then fractionally distilled through an 18 inch packed column.

| Fraction No. | Boiling Range, °C | Pressure, mm Hg | Weight, grams |
|---|---|---|---|
| 1 | 31–72 | atmospheric | 96.0 |
| 2 | 72–119 | atmospheric | 11.4 |
| 3 | 119–121 | atmospheric | 23.2 |
| Residue | — | — | 8.0 |

Analysis of the fractions, including the residue, by GLC showed that the product mixture was comprised of:

| | |
|---|---|
| Methanol | 13.9 g |
| 3-Methyl-3-buten-1-ol | 15.6 g |
| Methyl formate (recovered) | 76.5 g |
| 3-Methyl-3-buten-1-yl formate | 25.5 g |

Based on the amount of formaldehyde charged to the reactor the yield of the unsaturated ester was 45.2% of the theoretical yield.

EXAMPLE IV

A one liter autoclave was charged with 22 g (0.692 mol) of 94.4% paraformaldehyde, 250 ml (225 g, 2.55 mols) ethyl acetate and 235 g (5.595 mols) of propylene. The reactor was heated for 3 hours at 225°C (pressure was 3100–2850 psig). The reactor was cooled, vented, opened and the contents filtered into a distillation flask.

The product mixture was then fractionally distilled through a 24 inch packed column.

| Fraction No. | Boiling Range, °C | Pressure, mm Hg | Weight, grams |
|---|---|---|---|
| 1 | 62–77 | atmospheric | 230.7[a] |
| 2 | 77–100 | atmospheric | 29.0 |
| Residue | — | — | 2.0 |

[a] Some unreacted formaldehyde was detected.

GLC analysis of the fractions indicated that at least two products were formed in the reaction which were presumed to be 3-buten-1-yl acetate and 3-buten-1-ol. No further characterization of the reaction mixture was attempted.

I claim:

1. A process for the production of unsaturated esters which comprises reacting
   a. at least one olefinic reactant containing from 3–20 carbon atoms per molecule and having at least one allylic hydrogen atom in the molecule and such olefinic reactants having substituent groups selected from —CN, —CO$_2$CH$_3$, —Cl, —F, and —O—CH$_3$ which are attached to a carbon atom which is at least 2 carbon atoms removed from a carbon atom of the double bond with
b. formaldehyde in the presence of
c. at least one saturated ester reactant diluent of the general formula

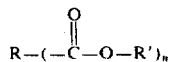

wherein $n$ is an integer of 1 or 2 and wherein if $n$ is 1, R is hydrogen or a hydrocarbon radical selected from alkyl, aryl, cycloalkyl, and combinations thereof, and wherein if $n$ is 2, R is a divalent hydrocarbon radical selected from alkylene, arylene, cycloalkylene, and combinations thereof, and further wherein if R is not hydrogen the hydrocarbon radical contains from 1–12 carbon atoms and R' is a hydrocarbon radical having from 1–10 carbon atoms, said reacting being carried out at a molar ratio of (a) to (b) of at least 1 to 1 and a molar ratio of (c) to (b) of at least 0.5 to 1 under reaction conditions of elevated temperature sufficient to form unsaturated esters.

2. A process according to claim 1 wherein said reacting is carried out at a temperature in the range of about 50° to about 350°C under autogenous pressure and a molar ratio of (a) to (b) of 5/1 to 10/1 and a molar ratio of (c) to (b) of 2/1 to 10/1.

3. The process of claim 1 which consists essentially in heating isobutylene with paraformaldehyde in the presence of methyl benzoate at a temperature in the range of about 200° to about 300°C to form 3-methyl-3-buten-1-yl benzoate.

4. The process of claim 1 which consists essentially in heating isobutylene with paraformaldehyde in the presence of methyl formate at a temperature in the range of about 200° to about 300°C to form 3-methyl-3-buten-1-yl formate.

5. The process of claim 1 which consists essentially in heating propylene with paraformaldehyde in the presence of ethyl acetate at a temperature in the range of about 200° to about 300°C to form 3-buten-1-yl acetate.

* * * * *